United States Patent
Nicolodi et al.

(12)

(10) Patent No.: US 6,608,088 B1
(45) Date of Patent: Aug. 19, 2003

(54) USE OF DONEREZIL FOR THE TREATMENT OF FUNCTIONAL AND/OR ORGANIC PAIN SYNDROMES

(75) Inventors: Maria Nicolodi, Fiesole (IT); Federigo Sicuteri, Fiesole (IT)

(73) Assignee: Eisai., Ltd., Tokyo (JP)

( * ) Notice: Subject to any disclaimer, the term of this patent is extended or adjusted under 35 U.S.C. 154(b) by 0 days.

(21) Appl. No.: 09/763,751

(22) PCT Filed: Sep. 9, 1999

(86) PCT No.: PCT/EP99/06648

§ 371 (c)(1),
(2), (4) Date: May 7, 2001

(87) PCT Pub. No.: WO00/15205

PCT Pub. Date: Mar. 23, 2000

(30) Foreign Application Priority Data

Sep. 11, 1998 (IT) ............................................. FI98A0208

(51) Int. Cl.[7] ............................................. A61K 31/445
(52) U.S. Cl. ......................................................... 514/319
(58) Field of Search .................................. 514/129, 319, 514/490

(56) References Cited

U.S. PATENT DOCUMENTS 5,010,083 A   4/1991   Allen et al.

FOREIGN PATENT DOCUMENTS

| EP | A1413667  | 2/1991  |
| EP | A1515302  | 11/1992 |
| WO | A1-9729750 | 8/1997 |
| WO | A1-9908672 | 2/1999 |

OTHER PUBLICATIONS

Buerkle et al, Chemical Abstracts, vol. 129, abstract No. 104116, 1998.*
Yang et al., Chemical Abstracts, vol. 128, abstract No. 226155, 1998.*
Ikonomoff, Schweizer Archiv. Zur Neurologie, vol. 102, No. 2, pp. 299–312.
Dawson et al., Behavioural Brain Research, vol. 57, No. 2, pp. 143–153 (1993).
Bryson et al., Drugs Aging, vol. 10, No. 3, pp. 234–239 (1997).
Nicolodi et al., Int'l Jour. of Pshycol., vol. 30, No. 1–2, p. 239 (1998),
Press et al., Expert Opinion on Therapeutic Patents, vol. 4, No. 4, pp. 379–393 (1994).
Abram et al. Anesthesia and Analgesia, vol. 81, No. 3, pp. 501–507 (1995).

* cited by examiner

*Primary Examiner*—William R. A. Jarvis
(74) *Attorney, Agent, or Firm*—Birch Stewart Kolasch & Birch LLP

(57) ABSTRACT

Methods of use of donepezil having central action for the treatment of function (migraine and primary fibromyalgia) and/or organic (amputation, "phantom limb", tumoral or traumatic denervation or autoimmune mechanism) central pain syndromes are disclosed.

9 Claims, 3 Drawing Sheets

USE OF DONEREZIL FOR THE TREATMENT OF FUNCTIONAL AND/OR ORGANIC PAIN SYNDROMES

This application is the national phase under 35 U.S.C. §371 of PCT International Application No. PCT/EP99/06648 which has an International filing date of Sep. 9, 1999, which designated the United States of America.

FIELD OF THE INVENTION

The present invention refers to the use of acetylcholinesterase inhibitors with high specificity and selectivity for centrally active acetylcholinesterase (resulting in an increased concentration and duration of acetylcholine in brain) for preparing pharmaceutical compositions for the treatment of functional (migraine and primary fibromyalgia) and/or organic ("phantom limb" caused by tumoral or traumatic denervation or autoimmune mechanism) central pain syndromes.

BACKGROUND OF THE INVENTION

Along the years migraine has been the object of deep interest and studies in view of the importance of this pathology both for the extremely large number of patients involved and because it causes (during its more serious episodes) important or total limitations to otherwise healthy subjects.

Various theories were formulated in order to find an explanation to the origin of migraine. Among these theories we can remember the "dry theory" (according to which the pain is due to the pulsing distension of cephalic vessels), the "Wet theory" (which implies the sterile inflammation of the arterial vessels which became dilated and bloated), the "serotonin-theory" according to which the pathology is caused by a disorder of the serotoninergic system in the central nervous system.

This last theory was very successful and allowed the preparation of active principles having a serotonino-mimetic activity capable of relieving a migraine attack.

About thirty years ago an interesting article [Stoyan Iv. IKONOMOFF—Archives Suisses de Neurologie, Neurochirurgie et de Psychiatrie—Vol. 102, fascicule p. 299–312 (1968)] referred to the possibility of treating migraine by using pharmaceutical products, such as Nivaline, an alkaloid, and Syntostigmine, which were known for their acetylcholinesterase inhibiting effect.

The article proposed the use of the two above said compounds (or more generally of acetylcholinesterase inhibiting medicaments) as a possible new way for resolving migraine disorders. Unfortunately the use of the medicaments suggested in the above said word, as also of other similar compounds having the same effect, required very high dosages, the administration should be performed by injection and was responsible of various side effects which made their use difficult; therefore this way was abandoned and no indication was thereafter reported in the literature about the use of acetylcholinesterase inhibitors as medicament for the treatment of migraine. In fact even the most recent editions of fundamental text-books in Neurology and Pharmacology [see for example .Victor and Adams, McGraw-Hill, New York (last edition) and Goodman and Gilman, McGraw-Hill, New York (1996) respectively] do not report these drugs as employed or useful for treating pain, whatever its origin and mechanism.

Moreover in various studies [see for example C. Ghelardini et al.—Presynaptic auto- and hetero-receptors in the cholinergic regulation of pain—Trends In Receptor Research (Elsevier Science Publishers B.V.) (1992)] it is reported that peripherically active acetylcholinesterase inhibiting compounds are not suitable for analgesic use in man.

WO 97/29750 discloses the use of acetylcholine esterase inhibitors, including Donepezil or Metrifonate, for the treatment rheumatological diseases.

In H. M. Bryson et al.: Drugs Aging Vol. 10(3) 1997, pp. 234–239 and in G. R. Dawson et al.: Behavioural Brain Research, Vol. 57 (2) 1993, pp. 143–153, it is reported that analgesics, like morphine, can be used for causing disappearance or reduction of pain connected with disorders interesting the peripheral system.

EP-A-515302 describes the treatment of fatigue syndrome with cholinesterase inhibitor.

In EP-A413667 and U.S. Pat. No. 5,010,083 several compounds for the alleviating of pain and memory dysfunction are described.

In J. B. Press et al.: Expert Opinion Vol. 4(4), 1994, pp. 379–393 an up-date of the studies regarding opioic and non-opioid analgesia is reported.

BRIEF SUMMARY

It was now surprisingly found that acetycholinesterase inhibiting compounds with high specificity and selectivity for centrally active acetylcholinesterase can be used with excellent results in the acute, abortive or preventive, prophylactic treatment of migraine and also of other related disorders which are commonly defined as functional and/or organic neurogenic central pain syndromes.

Furthermore, the acetylcholinesterase inhibiting compounds with high specificity and selectivity for centrally active acetylcholinesterase in the present invention is defined as follows: the acetylcholinesterase inhibiting compounds having clinical indication of use such as central progressive memory deterioration in Alzheimer disease or senile dementia and which can cross the blood-brain barrier and can enter the brain in large amounts.

Other anticholinesterase agents can not be useful for treating CNS cholinergic disturbances due to acting peripheral tissues including sympathetic ganglia. Among the above said pathologies we can remember: migraine, primary fibromyalgia, pain syndromes from organic deafferentation caused by amputation ("phantom limb"), denervation or autoimmune mechanism (multiple sclerosis) or infections (zosteric postherpetic nevralgia).

DETAILED DESCRIPTION OF THE INVENTION

The acetylcholinesterase inhibitors according to the invention as above defined do not present the undesired side effects as miosis and block of accomodation reflex with resultant focusing problems in near vision, changes in the function of all the secretory glands, including lacrimal, bronchial, sweat, salivary, antral, intestinal, and acinar pancreatic glands, nausea, vomit, gastric acid hyper-secretion, abdominal pains, diarrhoea, fainting or pre-fainting sensation, disturbances of cardio-vascular functions. The administration is well tolerated by patients and allows to obtain the desired results even with a single oral administration daily.

The present invention obviously refers to pharmaceutical compositions containing as active principle an acetylcholinesterase inhibitor having central activity possibly in combination with the usual excipient used for preparing pharmaceutical composition for oral administration for the treatment of the above said pathologies.

In particular the compositions according to the invention will contain the active principle in quantities comprised between 1.5–12 mg, more preferably 5–10 mg.

The treatment can be symptomatic or chronic.

The symptomatic, acute treatment is normally performed by administering orally to the patient a single dosage containing from 0.1 to 50 mg daily, preferably 0.5 to 40 mg daily, more preferably 1 to 30 mg daily of active principle; while for the chronic treatment the same administration can be repeated once a day for 40–80 days.

Among the compounds useful according to the present invention particularly preferable are: Donepezil or a pharmacologically acceptable salt thereof, Rivastigmine or a pharmacologically acceptable salt thereof and Metrifonate.

These compounds are shown hereinafter:
Donepezil
1H-Inden-1-one, 2,3-dihydro-5,6-dimethoxy-2-[[1-(phenylmethyl)4-piperidinyl]methyl]-, hydrochloride
[Hydrochloride: CAS Registry No. 120011-70-3]

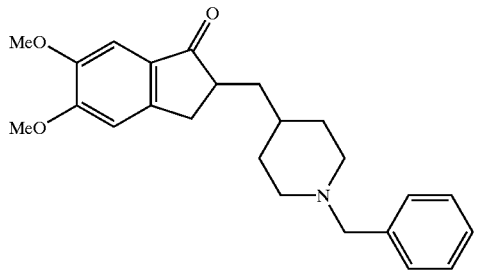

(2) Rivastigmine
Carbamic acid, ethylmethyl-, 3-[1-(dimethylamino)ethyl] phenyl ester
[CAS Registry No. 123441-03-2]

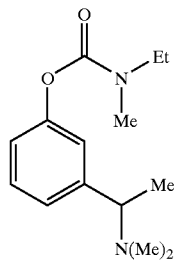

(3) Metrifonate
Phosphoric acid, (2,2,2-trichloro-1-hydroxyethyl)-, dimethyl ester
[CAS Registry No. 52-68-6]

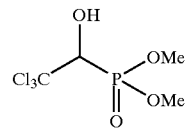

In the present invention, the term "pharmacologically acceptable salt thereof" include the salts of inorganic acids, such as hydrochloride, hydrobromide, sulfate, nitrate and phosphate, and those of organic acids, such as formate, acetate, oxalate, succinate, maleate, fumarate, methanesulfonate, benzenesulfonate and toluenesulfonate. Among these, hydrochloride is more preferable.

In practising the present invention, the acetylcholinesterase inhibitor compounds of the present invention may be orally or parentally administered. In general, the are administered in the form of tablet, granule, capsule and syrup, and in the form of injection, such as intravenous, subcutaneous and intramuscular injection, suppositories or sublingual tablets.

The dose will vary depending upon the symptom, age, sex, body weight, sensitivity of patients, method of administration, time and interval of administration and property, dispensing, and kind of pharmaceutical preparations, kind of effective ingredients, etc.

Pharmaceutical preparations in the form of, e.g., tablet, granule, capsule, syrup, injections are prepared according to the usual manner.

Experimental Data

Migraines

Various groups of patients suffering from different kind of migraine were treated with 5 mg of Donepezil hydrochloride daily.

The results are reported in the following histograms 1 to 6 (see FIGS. 1–6).

Figure 1:
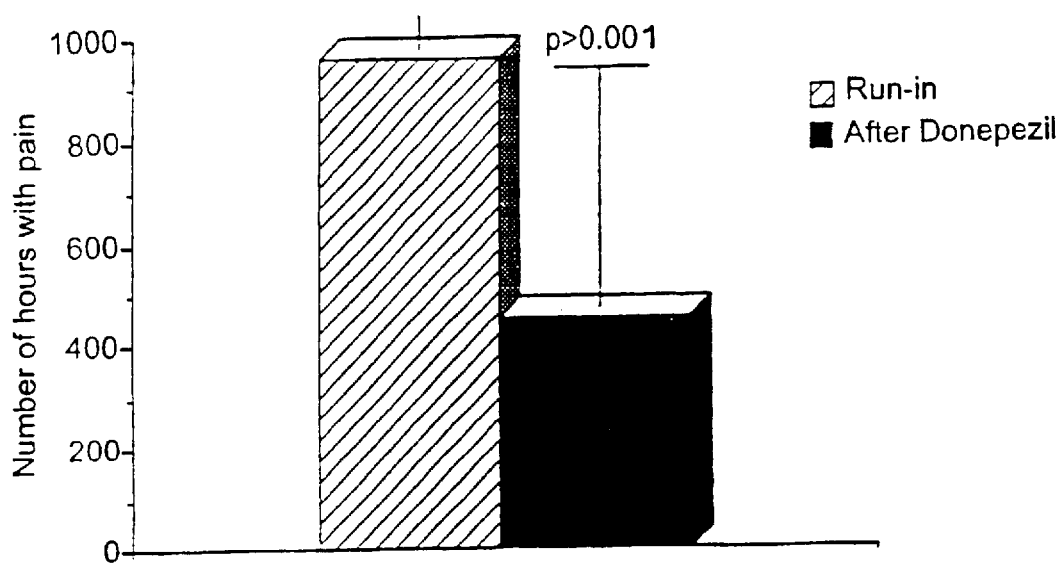
FIG. 1—Shows the number of hours with pain before and after 60 days chronic treatment with Donepezil hydrochloride (5 mg/die) measured in tests on 17 patients suffering from chronic migraine, otherwise known as "transformed migraine" (International Headache Society criteria).
Figure 2:
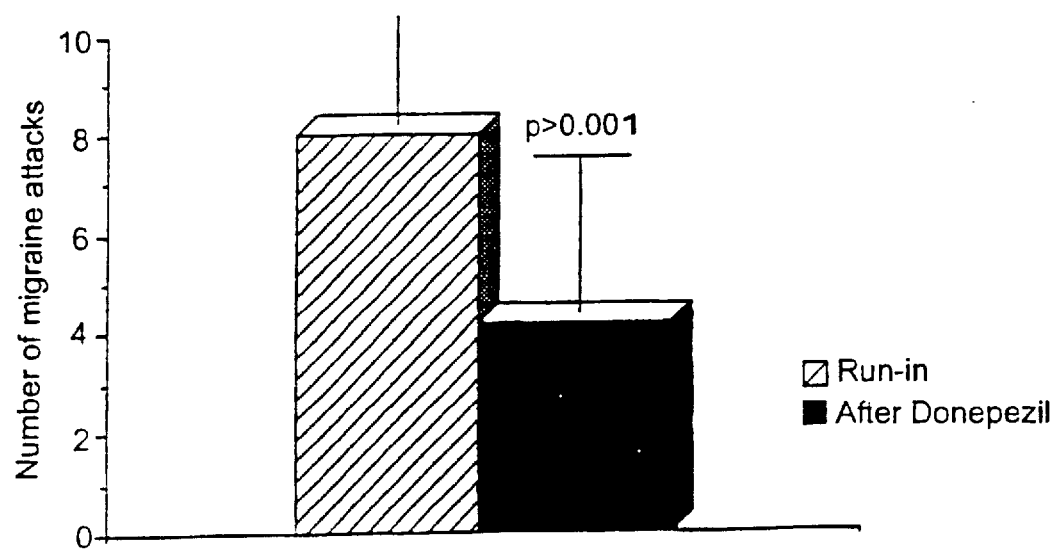
FIG. 2—Shows the number of migraine attacks before and after chronic Donepezil hydrochloride treatment (5 mg/die) for the above said group of patients.
Figure 3:
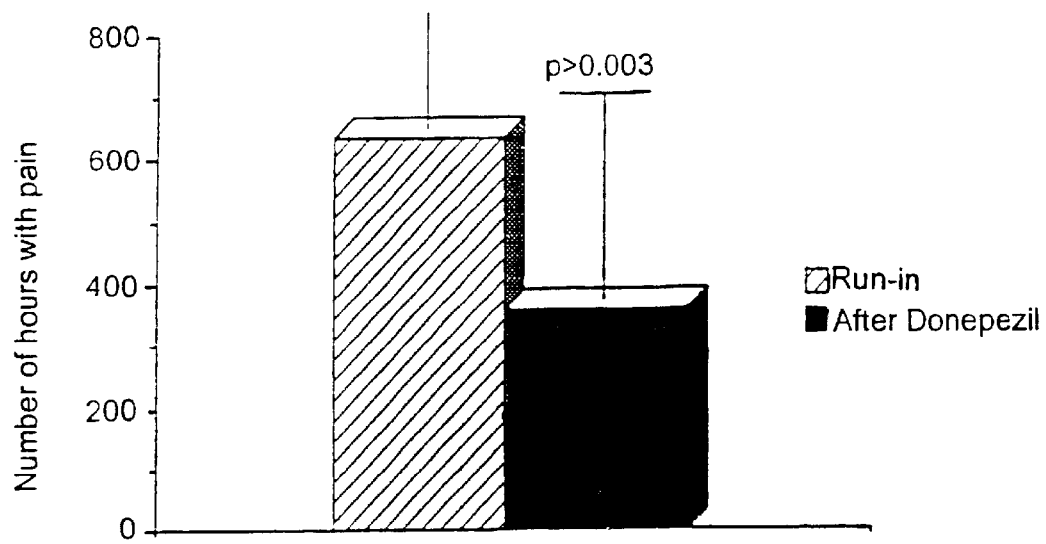
FIG. 3—Shows the number of hours with pain before and after chronic treatment with Donepezil hydrochloride (5 mg/die) measured in tests on 18 patients suffering from migraine without aura.
Figure 4:
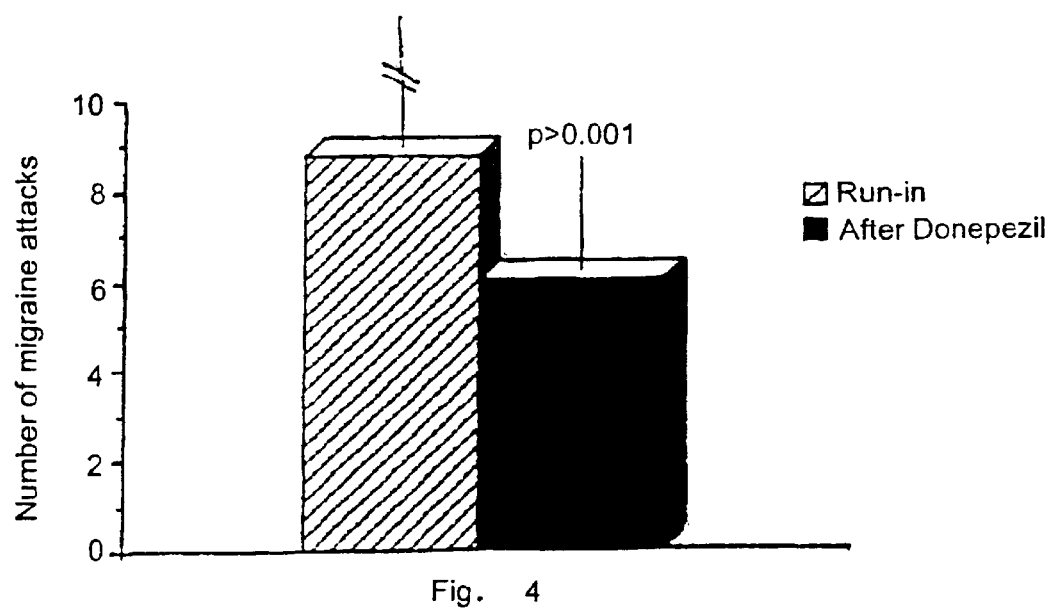
FIG. 4—Shows the number of migraine attacks before and after Donepezil hydrochloride treatment (5 mg/die) for the same group of patients as in FIG. 3.
Figure 5:
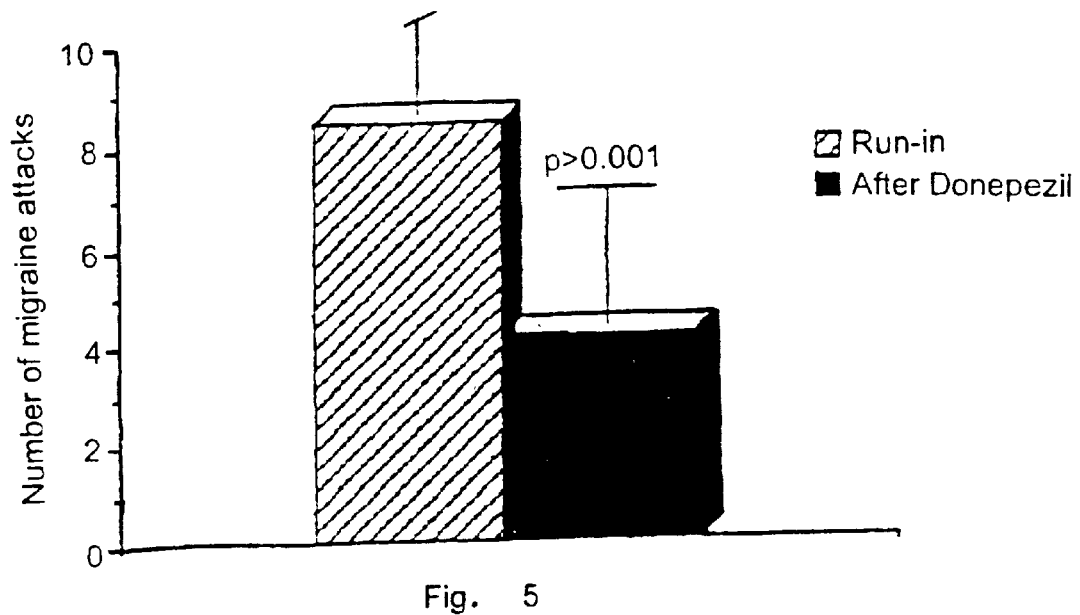
FIG. 5—Shows the results of prophylaxis of migraine with Donepezil hydrochloride reporting the number of migraine attacks following 60 days run-in and 60 days treatment in 35 patients suffering from severe migraine without aura.
Figure 6:
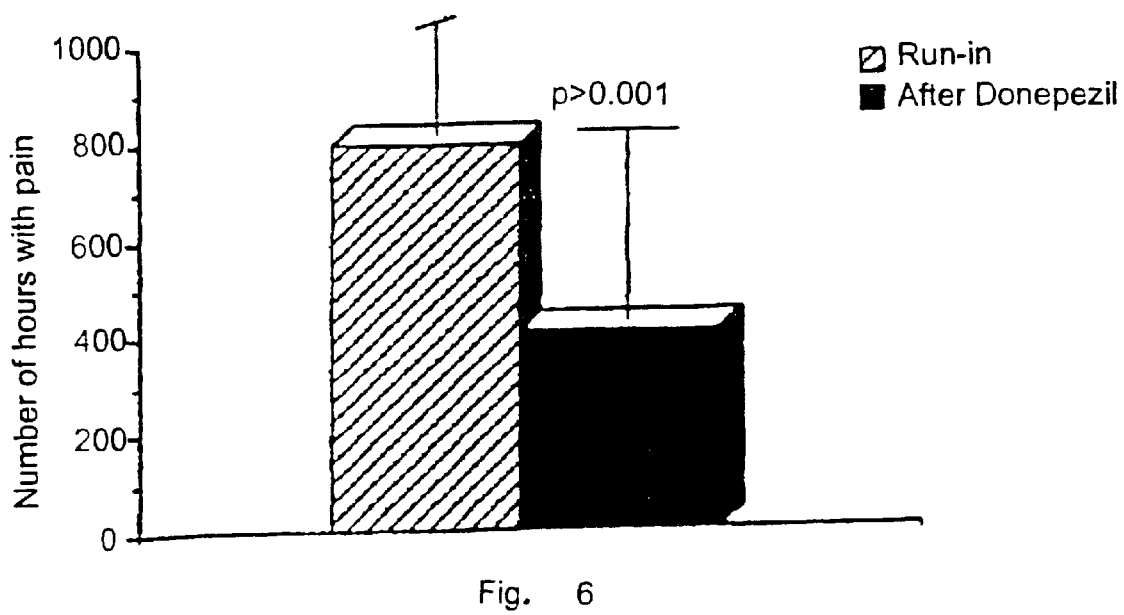
FIG. 6—Shows the results of prophylaxis of migraine with Donepezil hydrochloride reporting the hour with pain following 60 days run-in and 60 days treatment for the same group of patients as in FIG. 5.

Moreover, 8 patients suffering from migraine attacks longer than 72 h were treated with 20 mg of Donepezil hydrochloride acutely given, also in this case the results were highly satisfactory.

Primary Fibromyalgia

Systemic pain of muscles, tendons, viscera (oesophagus, stomach, colon); these syndromes are considered particularly difficult to hale.

Tests performed on 16 patents (same conditions as those described for the migraine tests) showed an improvement of the patient's conditions in 60% of the cases treated and total disappearance of the pain in 10% of the cases.

Pain Syndromes Caused by Denervation

In the pain syndromes caused by denervation or amputation pain develops on the limb or body part which is denervated and therefore is insensible to nociceptive stimuli ("painful anaesthesia").

Nine patients who had no advantages after treatment with antiinflammatory analgesica or opioids were tested in the same conditions as above described.

Five patients showed an improvement of their conditions of 50–80%.

All patients showed an high tolerance to the treatment, with side effects much lower then those observed in the case of administration of the commonly available acute and prophylactic therapies for curing migraine and central neurogenic pain.

What is claimed is:

1. A method of treating pain, functional pain syndromes, or organic pain syndromes in a patient comprising administering a pharmaceutically effective amount of an acetylcholinesterase inhibitor with high specificity and selectivity for centrally active acetylcholinesterase to a patient in need thereof wherein the acetylcholinesterase inhibitor is Donepezil or a pharmaceutically acceptable salt thereof, and wherein the pain, functional pain syndromes, or organic pain syndromes are selected from the group consisting of migraine, primary fibromyalgia, and pain syndromes due to amputation ("phantom limb");

and the pain results from tumoral denervation, traumatic denervation, or autoimmune mechanism.

2. The method of claim 1, wherein the acetylcholinesterase inhibitor is in a form suitable for oral administration.

3. The method of claim 1, wherein the acetylcholinesterase inhibitor is administered in a dose of 1 to 30 mg.

4. The method of claim 1, wherein the acetylcholinesterase inhibitor is administered orally, daily in a dose of 1 to 30 mg.

5. The method according to claim 4 wherein the treatment is relief from pain.

6. The method according to claim 4 wherein the treatment is prevention of pain attack.

7. The method according to claim 4 wherein the treatment is chronic and prolonged for 40–80 days.

8. The method claimed in claim 1, wherein acetylcholinesterase inhibitor administered in a daily dose of from 0.1 to 50 mg.

9. The method claimed in claim 8, wherein acetylcholinesterase inhibitor administered in a daily dose of from 1 to 30 mg.

* * * * *